United States Patent
Hsieh et al.

(10) Patent No.: US 11,696,964 B2
(45) Date of Patent: Jul. 11, 2023

(54) ULTRAVIOLET DEVICE

(71) Applicant: Soulnano Limited, Wanchai (HK)

(72) Inventors: Hung-Hsin Hsieh, Kaohsiung (TW); Cho-Hang Wong, Shatin (HK)

(73) Assignee: SOULNANO LIMITED, Wanchai (HK)

(*) Notice: Subject to any disclaimer, the term of this patent is extended or adjusted under 35 U.S.C. 154(b) by 348 days.

(21) Appl. No.: 17/166,185

(22) Filed: Feb. 3, 2021

(65) Prior Publication Data
US 2021/0308298 A1    Oct. 7, 2021

Related U.S. Application Data

(60) Provisional application No. 63/005,530, filed on Apr. 6, 2020.

(30) Foreign Application Priority Data

Jul. 30, 2020   (TW) .................. 109125844

(51) Int. Cl.
| | | |
|---|---|---|
| *A61L 2/10* | (2006.01) | |
| *A61L 2/18* | (2006.01) | |
| *A61L 2/26* | (2006.01) | |
| *A61L 2/20* | (2006.01) | |

(52) U.S. Cl.
CPC .................. *A61L 2/10* (2013.01); *A61L 2/18* (2013.01); *A61L 2/20* (2013.01); *A61L 2/26* (2013.01); *A61L 2202/11* (2013.01); *A61L 2202/122* (2013.01); *A61L 2202/15* (2013.01)

(58) Field of Classification Search
CPC ..... A61L 2/10; A61L 2/18; A61L 2/20; A61L 2/26; A61L 2202/21; A61L 2202/11; A61L 2202/122; A61L 2202/15
USPC .................................................. 250/504 R
See application file for complete search history.

(56) References Cited

U.S. PATENT DOCUMENTS

| | | | | |
|---|---|---|---|---|
| 5,215,588 A | * | 6/1993 | Rhieu | C23C 16/45519 427/583 |
| 2004/0168742 A1 | * | 9/2004 | Kim | H01L 21/67017 141/98 |
| 2021/0177999 A1 | * | 6/2021 | Ogihara | G01J 5/0025 |
| 2021/0395880 A1 | * | 12/2021 | Kato | C23C 16/45565 |

* cited by examiner

*Primary Examiner* — Nicole M Ippolito
(74) *Attorney, Agent, or Firm* — Locke Lord LLP; Tim Tingkang Xia, Esq.

(57) ABSTRACT

An ultraviolet device is provided, which includes a gas jetting module, a flow rate adjustment module, an ultraviolet module and a first gas channel. The gas jetting module includes an upper panel, a lower panel and a frame. The upper panel is disposed on the upper side of the frame. The lower panel is disposed on the lower side of the frame and includes one or more gas outlets. A gas chamber is formed between the upper panel, lower panel and frame. The first gas channel is connected to the gas jetting module. The flow rate adjustment module is connected to the first gas channel and adjusts the flow rate of the gas inputted into the gas chamber via the first gas channel. The ultraviolet module includes an ultraviolet light source and is connected to the gas jetting module.

20 Claims, 12 Drawing Sheets

ULTRAVIOLET DEVICE

CROSS REFERENCE TO RELATED APPLICATION

All related applications are incorporated by reference. The present application is based on, and claims priority from, U.S. Provisional Application No. 60/005,530, filed on Apr. 6, 2020, and Taiwan Application Serial Number 109125844, filed on Jul. 30, 2020, the disclosures of which are hereby incorporated by reference herein in its entirety.

TECHNICAL FIELD

The technical field relates to an ultraviolet device, in particular to a cost-effective ultraviolet device.

BACKGROUND

Ultraviolet (UV) LED was commercialized in recent years. UV LED has already replaced a lot of UV mercury lamps in many UV curing devices because of its advantage of lower power consumption. Although currently available UV curing devices with UV LEDs can achieve lower power consumption, but cannot effectively solve the problem of oxygen inhibition, which affects the UV curing quality of the currently available UV curing devices. However, there is no solution for the currently available UV curing devices to solve the problem.

Since the curing object is moving, air can follow the pathway of the curing target to enter the space between the UV curing device and the target. For the reason, it is impossible to create a closed-loop environment in an UV curing process. Besides, a closed-loop environment cannot be created only when the whole working space is a closed-loop environment. Moreover, creating a closed-loop environment would significantly increase cost, which is not a cost-effective solution.

Another way to improve UV curing quality is to inhibit oxygen by inputting gas (e.g. nitrogen, helium, argon, carbon dioxide, etc.). However, fulling up the working space with gas would also significantly increase cost, which is not a cost-effective solution.

SUMMARY

An embodiment of the disclosure relates to an ultraviolet device, which includes a gas jetting module, a flow rate adjustment module, an ultraviolet module and a first gas channel. The gas jetting module includes an upper panel, a lower panel and a frame. The upper panel is disposed on the upper side of the frame. The lower panel is disposed on the lower side of the frame and includes a gas outlet. A gas chamber is formed between the upper panel, the lower panel and the frame. The first gas channel is connected to the gas jetting module and inputting the gas into the gas chamber. The flow rate adjustment module is connected to the first gas channel and adjusts the flow rate of the gas inputted into the gas chamber. The ultraviolet module includes an ultraviolet light source, and the ultraviolet module is disposed on the gas jetting module and connected to the gas jetting module. The ultraviolet light generated by the ultraviolet light source is radiated in a first direction after the ultraviolet light passes through the upper panel and the lower panel, and the gas is jetted out of the gas outlet in the first direction.

Another embodiment of the disclosure relates to an ultraviolet device, which includes a gas jetting module, an ultraviolet module and a flow rate adjustment module. The gas jetting module includes a panel and a frame. The panel is disposed on the lower side of the frame and includes a gas outlet. The ultraviolet module includes an ultraviolet light source and a first gas channel. The ultraviolet module is disposed on the upper side of the frame, and a gas chamber is formed between the ultraviolet module, the panel and the frame. The flow rate adjustment module is connected to the first gas channel and adjusts the flow rate of the gas inputted into the gas chamber. The ultraviolet light generated by the ultraviolet light source is radiated in a first direction after the ultraviolet light passes through the upper panel and the lower panel, and the gas is jetted out of the gas outlet in the first direction.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The disclosure will become more fully understood from the detailed description given herein below and the accompanying drawings which are given by way of illustration only, and thus are not limitative of the disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing. It should be understood that, when it is described that an element is "coupled" or "connected" to another element, the element may be "directly coupled" or "directly connected" to the other element or "coupled" or "connected" to the other element through a third element. In contrast, it should be understood that, when it is described that an element is "directly coupled" or "directly connected" to another element, there are no intervening elements.

Figure 1:
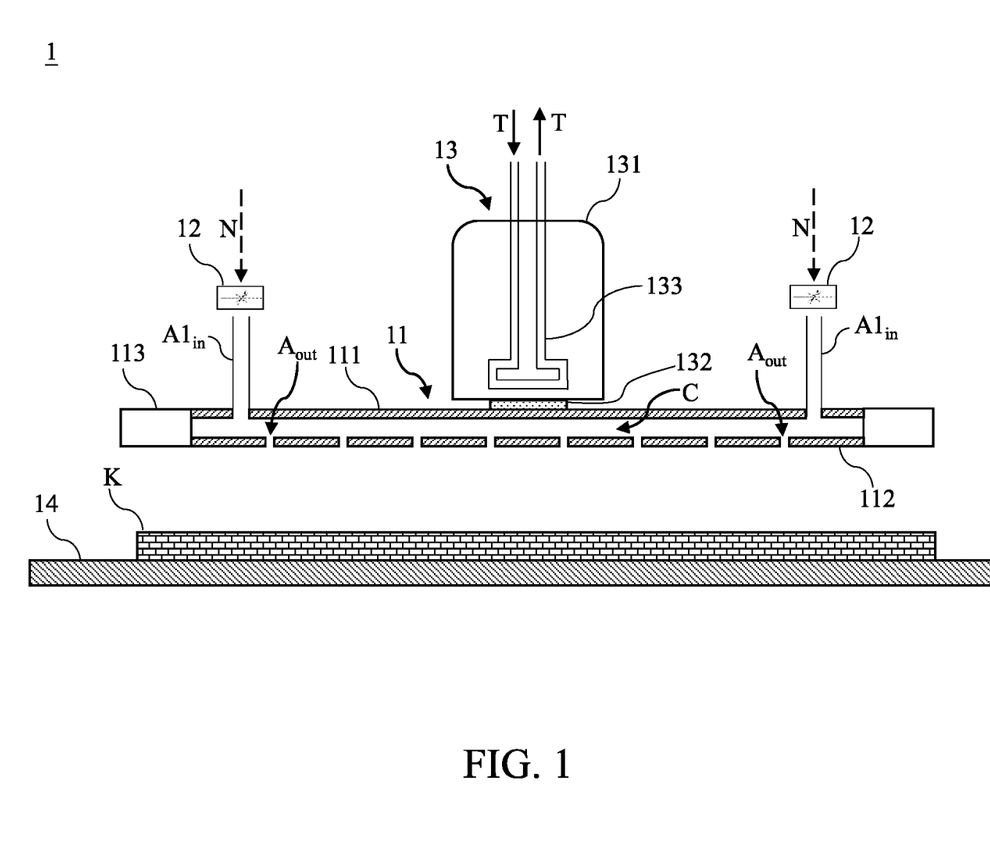
FIG. 1 is a front view of an ultraviolet (UV) device in accordance with a first embodiment of the disclosure.
Figure 2:
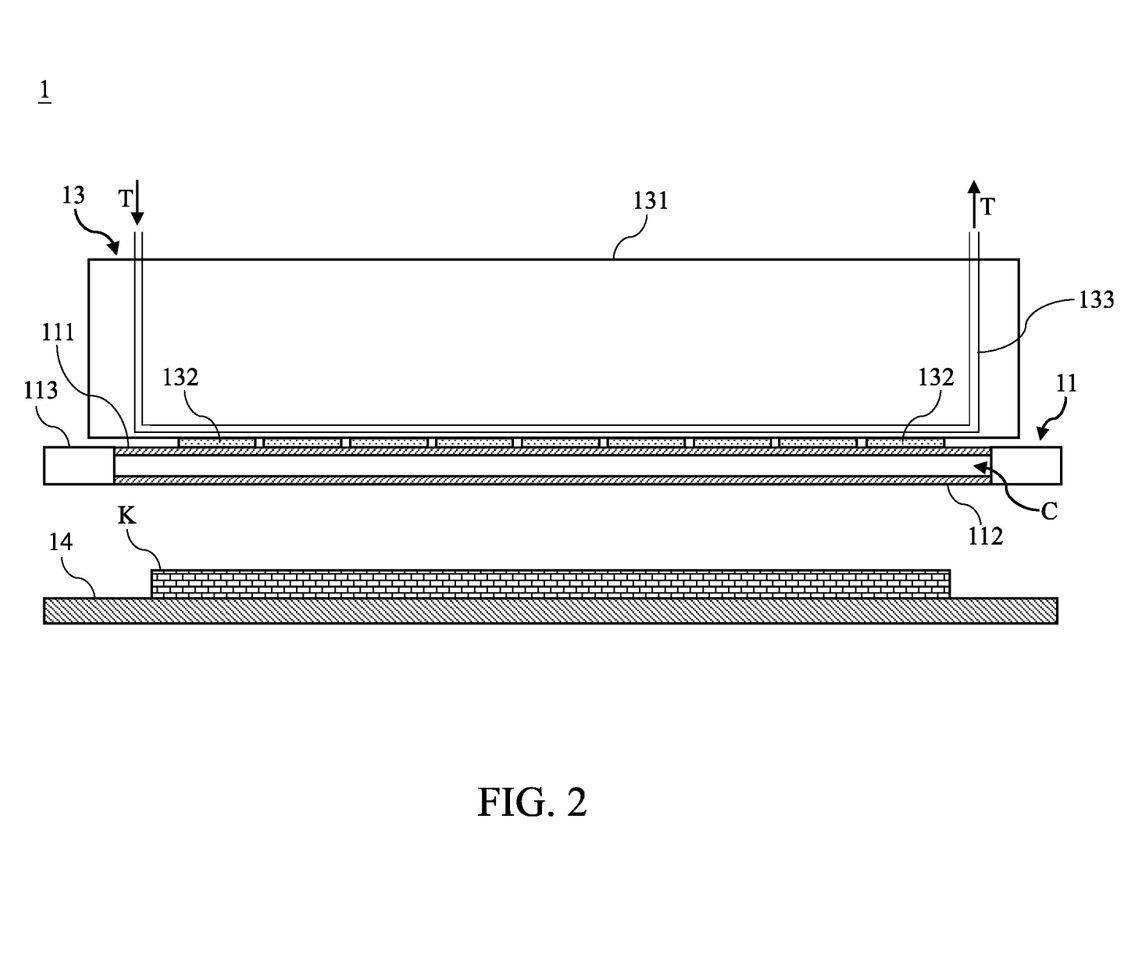
FIG. 2 is a side view of the UV device in accordance with the first embodiment of the disclosure.

Please refer to FIG. 1 and FIG. 2, which are a front view and a side view of an ultraviolet device in accordance with a first embodiment of the disclosure. As shown in FIG. 1 and FIG. 2, the ultraviolet (UV) device 1 includes a gas jetting module 11, a flow rate adjustment module 12 and an UV module 13.

The UV module 13 includes a housing 131, a plurality of UV light sources 132 and a coolant channel 133. The UV light sources 132 are disposed on the bottom of the housing 131 and may be arranged in straight line. In the embodiment, the UV light sources 132 may be UV LED arrays; in another embodiment, the UV light sources 132 may be UV mercury lamps or other similar light sources. The number of each of the above elements can be changed according to actual requirements; in another embodiment, the UV module 13 may have only one UV light source 132 or have several coolant channels 133. The coolant channel 133 is disposed inside the UV module 13; the coolant T flows in the inlet of the coolant channel 133 and then flows out of the outlet of the coolant channel 133 so as to cool the UV module 13. The UV light sources 132 and the other elements would generate a large amount of heat, and the coolant channel 133 can effectively cool the UV light sources 132 and the other elements, such that the UV module 13 can operate normally. In the embodiment, the coolant T may be a liquid coolant; in another embodiment, the coolant T may be a gaseous coolant.

In the embodiment, the gas jetting module 11 is a hollow and flat container, which includes an upper panel 111, a lower panel 112 and a frame 113. In another embodiment, the structure of the gas jetting module 11 may be modified according to actual requirements. In the embodiment, the upper panel 111 and the lower panel 112 may be made of glass, such as quartz glass. In another embodiment, the upper panel 111 and the lower panel 112 may be made of other proper transparent materials or UV-pass materials. The upper panel 111 is disposed on the upper side of the frame 113 and the lower panel 112 is disposed on the lower side of the frame 113, such that a gas chamber C is formed between the upper panel 111, the lower panel 112 and the frame 113. In the embodiment, the upper panel 111 and the lower panel 112 may be plane mirrors. In another embodiment, the upper panel 111 and the lower panel 112 may be concave mirrors, convex mirrors, spherical mirrors, aspherical mirrors, etc.

The UV device 1 further includes a plurality of first gas channels $A1_{in}$ and the first gas channels $A1_{in}$ are disposed on the upper panel 111 so as to connect to the gas chamber C. The lower panel 112 includes a plurality of gas outlets $A_{out}$ and the gas outlets $A_{out}$ are evenly distributed over the lower panel 112. The UV module 13 is disposed on the gas jetting module 11 and the UV light sources 132 of the UV module 13 contact the upper panel 111. In another embodiment, the UV device 1 may have only one first gas channel $A1_{in}$ and one gas outlet $A_{out}$. Similarly, the number of each of the above elements can be changed according to actual requirements.

The flow rate adjustment module 12 is connected to a gas storage tank (not shown in the drawings) and the first gas channels $A1_{in}$. The gas storage tank inputs the gas N into the first gas channels $A1_{in}$ and the flow rate adjustment module 12 adjusts the flow rate of the gas N inputted into the gas channel C. In the embodiment, the gas N may be nitrogen. In another embodiment, the gas N may be carbon dioxide or other inactive gases. In still another embodiment, the gas N may be an inert gas, such as helium, argon, etc.

The UV device 1 may further include a working table 14 and the working table 14 is under the gas jetting module 1. The user can put the curing object K on the working table 14 in order to perform the UV curing process. Besides, the working table 14 may have a conveyor belt or other similar structures so as to move the curing object K. In the embodiment, the curing object K may be a paper with ink (or varnish).

Figure 3A:
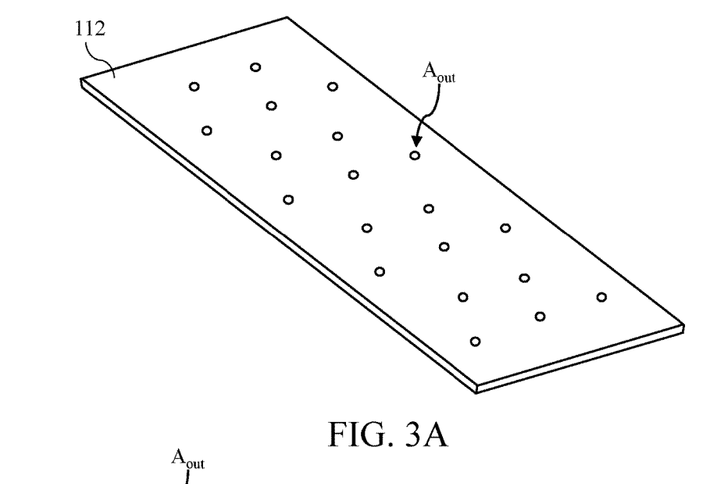
FIG. 3A and FIG. 3B are stereogram views of a lower panel of a gas jetting module of the UV device in accordance with the first embodiment of the disclosure.
Figure 3B:
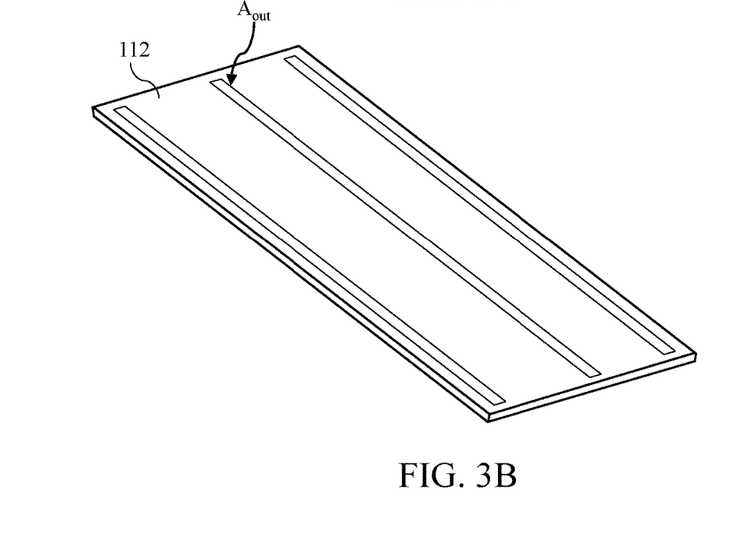

Please refer to FIG. 3A and FIG. 3B (not to scale), which are stereogram views of a lower panel of a gas jetting module of the UV device in accordance with the first embodiment of the disclosure. As shown in FIG. 3A, the gas outlets $A_{out}$ of the lower panel 112 may be holes. As shown in FIG. 3B, the gas outlets $A_{out}$ of the lower panel 112 may be gaps. In another embodiment, the structure of the lower panel 112 can be changed according to actual requirements.

Figure 4:
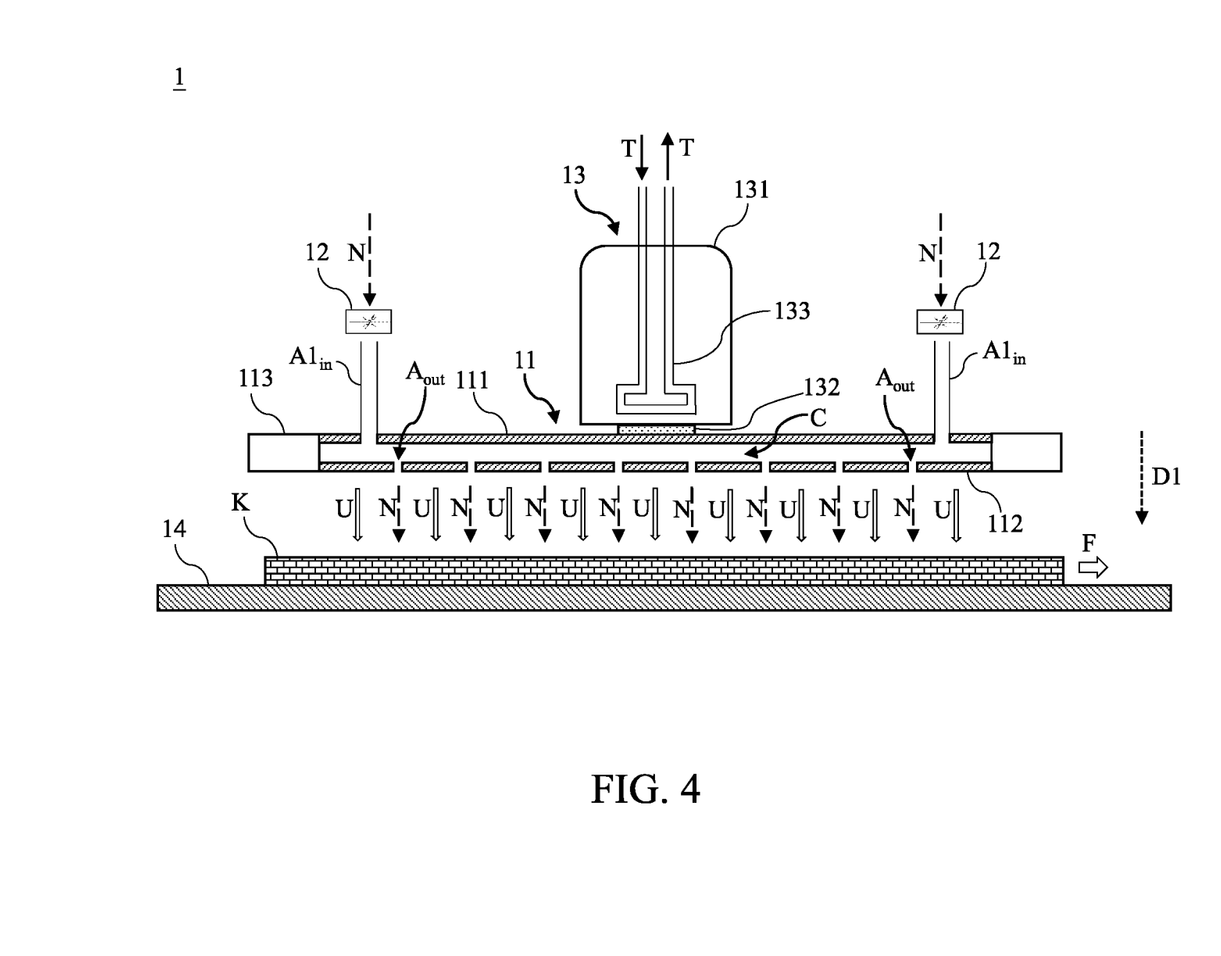
FIG. 4 is a schematic view of the UV device in operating status in accordance with the first embodiment of the disclosure.

Please refer to FIG. 4, which is a schematic view of the UV device in operating status in accordance with the first embodiment of the disclosure. As shown in FIG. 4, when the UV device 1 is activated, the working table 14 may move the curing object K in the direction of the arrow F. Then, the gas N is jetted out of the gas outlets $A_{out}$ in the first direction D1 to the surface of the curing object K in order to remove the air on the surface of the curing object K. Meanwhile, the UV light U generated by the UV light sources 132 of the UV module 13 is radiated in the first direction D1 after passing through the upper panel 111 and the lower panel 112.

Via the above mechanism, the air on the surface of the curing object K can be removed by the gas N jetted out of the gas outlets $A_{out}$ at the moment that the UV light U generated by the UV light sources 132 is radiated to the surface of the curing object K. Thus, the curing process of the ink on the surface of the curing object K would not be influenced by oxygen in the air, so the UV curing quality can be greatly improved. The user can properly adjust the flow rate of the flow rate adjustment module 12 in order to optimize the UV curing quality of the UV device 1.

In addition, as described above, the upper panel 111 and the lower panel 112 may be concave mirrors, convex mirrors, spherical mirrors, aspherical mirrors, etc. Accordingly, the upper panel 111 and the lower panel 112 can also provide light condensing, light diffusing or other functions to appropriately adjust the UV light U generated by the UV light sources 132 with a view to satisfy different requirements.

As set forth above, the UV device 1 can integrate the gas jetting module 11 with the UV module 13 by special design, so the UV device 1 can effectively inhibit oxygen in the UV curing process in order to remarkably improve the UV curing quality thereof.

Moreover, the gas jetting module 11 of the UV device 1 is a hollow and flat container, which can use the gas N by a highly efficient way. Accordingly, the UV device 1 can effectively inhibit oxygen in the UV curing process by a small amount of the gas N without creating a closed-loop environment, so can achieve the desired technical effect in a cost-effective way.

Furthermore, the UV device 1 is not only applicable to printing industry and other industries, but also effectively enhances the UV curing quality in a cost-effective way. Thus, the application of the UV device 1 can be more comprehensive.

The embodiment just exemplifies the disclosure and is not intended to limit the scope of the disclosure. Any equivalent modification and variation according to the spirit of the disclosure is to be also included within the scope of the following claims and their equivalents.

It is worthy to point out that the currently available UV device cannot provide an effective solution for oxygen inhibition, which affects the UV curing quality thereof. On the contrary, according to one embodiment of the present disclosure, the UV device integrates the gas jetting module with the UV module by special design, so the UV device can effectively inhibit oxygen in the UV curing process in order to significantly improve the UV curing quality thereof.

Besides, according to one embodiment of the present disclosure, the UV device integrates the gas jetting module with the UV module by special design, and can directly jet out inert gas or inactive gas to the surface of the curing object in order to remove air on the surface of the curing object. Thus, the UV device can effectively inhibit oxygen without creating a closed-loop environment, so can achieve the desired technical effect in a cost-effective way.

Further, according to one embodiment of the present disclosure, the UV device integrates the gas jetting module with the UV module by special design, and provide inert gas or inactive gas via the gas jetting module, which can greatly reduce the consumption of inert gas or inactive gas. There, the UV device can achieve the desired technical effect in a cost-effective way.

Moreover, according to one embodiment of the present disclosure, the UV device is applicable to various industries and can effectively enhance the UV curing quality in a cost-effective way. Thus, the application of the UV device can be more comprehensive. As described above, the UV device according to the embodiments of the disclosure can actually achieve unpredictable technical effects.

Figure 5:
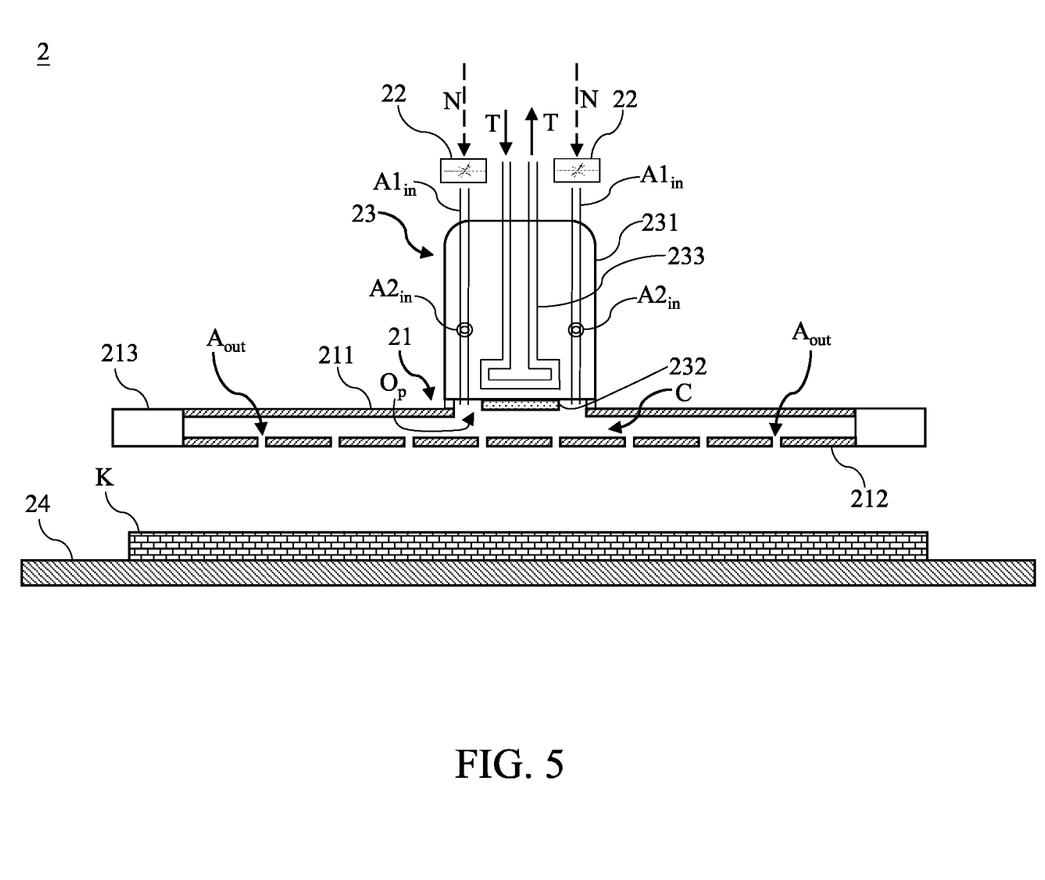
FIG. 5 is a front view of an UV device in accordance with a second embodiment of the disclosure.
Figure 6:
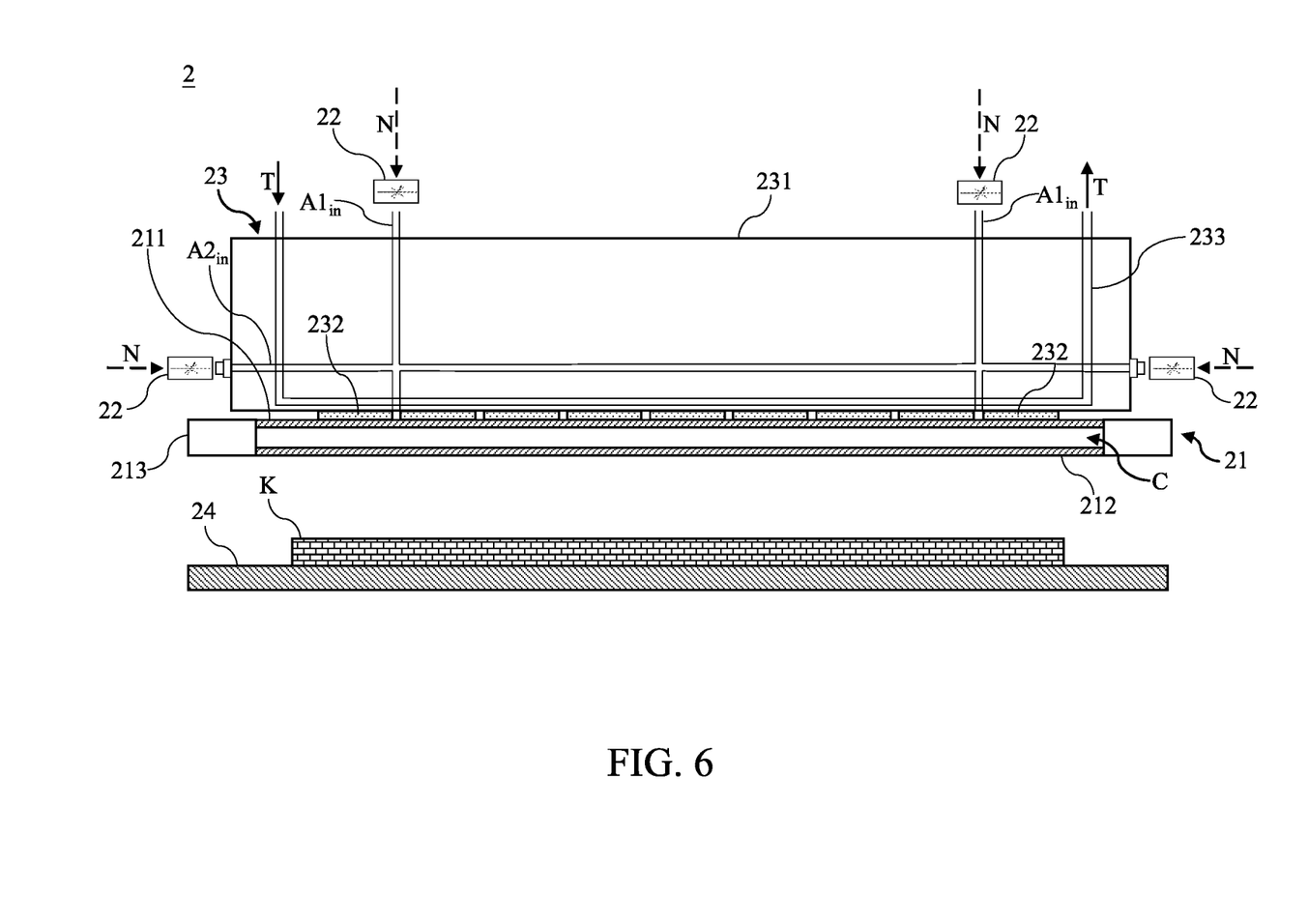
FIG. 6 is a side view of the UV device in accordance with the second embodiment of the disclosure.

Please refer to FIG. 5 and FIG. 6, which are a front view and a side view of an ultraviolet device in accordance with a first embodiment of the disclosure. As shown in FIG. 5 and FIG. 6, the ultraviolet (UV) curing device 2 includes a gas jetting module 21, a flow rate adjustment module 22 and an UV module 23.

The UV module 23 includes a housing 231, a plurality of UV light sources 232, a coolant channel 233, a plurality of first gas channels $A1_{in}$ and a plurality of second gas channels $A2_{in}$. Similarly, the number of each of the above elements can be changed according to actual requirements. In another embodiment, the UV module 23 may have only one UV light source 232, one first gas channel $A1_{in}$ and one second gas channel $A2_{in}$, or have several coolant channels 233. The UV light sources 232 are disposed on the bottom of the housing 231 and may be arranged in straight line. The coolant channel 233 is disposed inside the UV module 23; the coolant T flows in the inlet of the coolant channel 233 and then flows out of the outlet of the coolant channel 233 so as to cool the UV module 23. Each of the first gas channels $A1_{in}$ extends from the top surface of the housing 231 to the bottom surface of the housing 231, such that the inlet of each of the first gas channels $A1_{in}$ protrudes from the top surface of the housing 231, and the outlet of each of the first gas channels $A1_{in}$ protrudes from the bottom surface of the housing 231. Each of the second gas channels $A2_{in}$ passes through the inner space of the housing 231, and extends from one side of the housing 231 to the other side of the housing 231 in order to connect to one or more the first gas channels $A1_{in}$. Accordingly, the gas N inputted from the second gas channels $A2_{in}$ can be exhausted from the outlets of the first gas channels $A1_{in}$.

In the embodiment, the gas jetting module 21 is a hollow and flat container, which includes an upper panel 211, a lower panel 212 and a frame 213. In another embodiment, the structure of the gas jetting module 21 may be modified according to actual requirements. The upper panel 211 is disposed on the upper side of the frame 213 and has an opening $O_p$. The lower panel 212 is disposed on the lower side of the frame 213 and includes a plurality of gas outlets $A_{out}$; the gas outlets $A_{out}$ are evenly distributed over the lower panel 212. In another embodiment, the UV device 2 may have only one gas outlet $A_{out}$; the number of the $A_{out}$ can be adjusted according to actual requirements. The UV module 23 is disposed on the gas jetting module 21 and connected to the opening $O_p$, such that a gas chamber C is formed between UV module 23, the upper panel 211, the lower panel 212 and the frame 213, and the outlets of the first gas channels $A1_{in}$ are connected to the gas chamber C. More specifically, the bottom of the UV module 23 may be connected to the opening $O_p$, such that the outlets of the first gas channels $A1_{in}$. and the UV light sources 232 are inside the opening $O_p$. In the embodiment, the upper panel 211 and the lower panel 212 may be plane mirrors. In another embodiment, the upper panel 211 and the lower panel 212 may be concave mirrors, convex mirrors, spherical mirrors, aspherical mirrors, etc.

The flow rate adjustment module 22 is connected to a gas storage tank (not shown in the drawings), the first gas channels $A1_{in}$ and the second gas channels $A1_{in}$. The gas storage tank inputs the gas N into the first gas channels $A1_{in}$ and the flow rate adjustment module 22 adjusts the flow rate of the gas N inputted into the gas channel C.

The UV device 2 may further include a working table 24 and the working table 24 is under the gas jetting module 2. The user can put the curing object K on the working table 24 in order to perform the UV curing process. Besides, the working table 24 may have a conveyor belt or other similar structures so as to move the curing object K. In the embodiment, the curing object K may be a paper with ink (or varnish).

Figure 7:
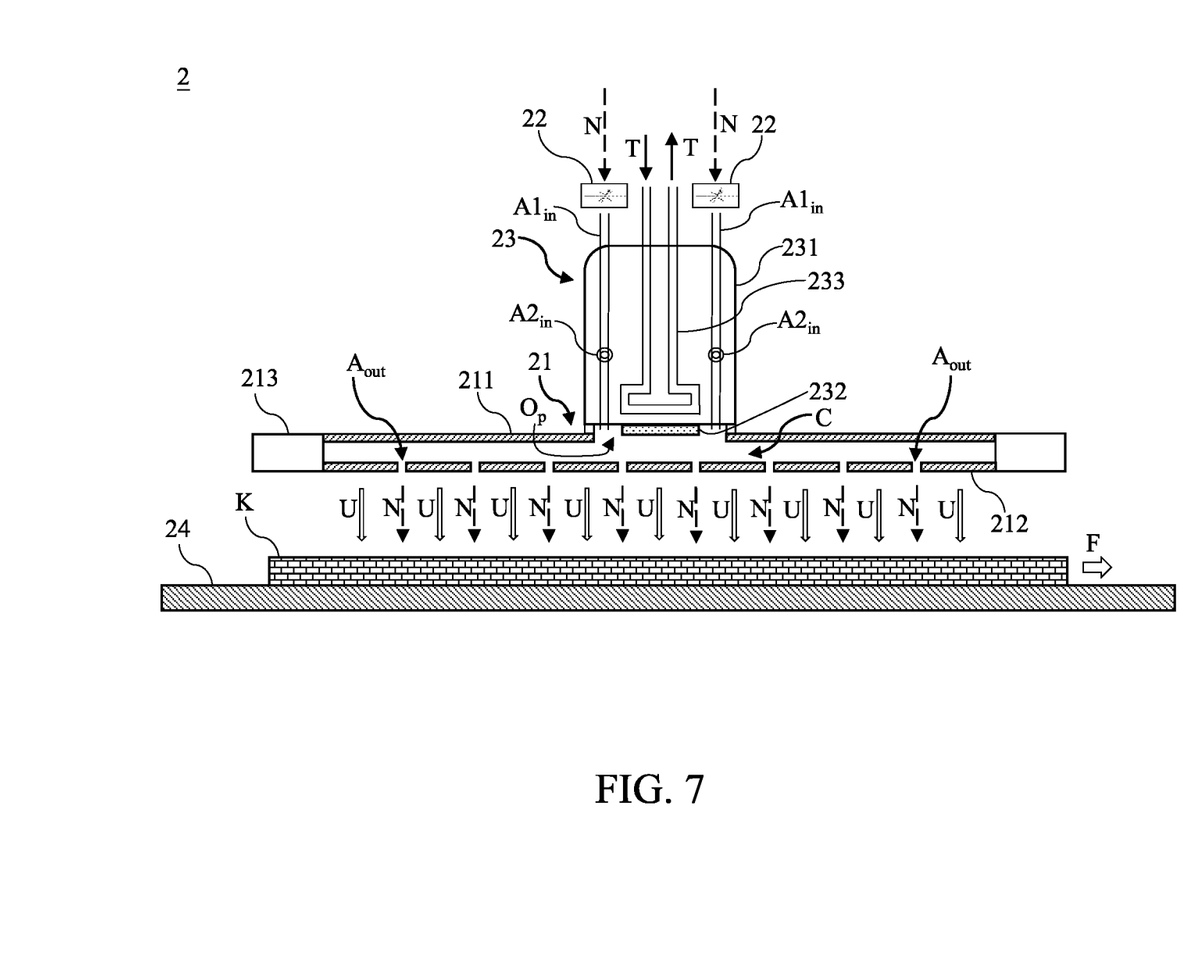
FIG. 7 is a schematic view of the UV device in operating status in accordance with the second embodiment of the disclosure.

Please refer to FIG. 7, which is a schematic view of the UV device in operating status in accordance with the second embodiment of the disclosure. As shown in FIG. 7, when the UV device 2 is activated, the working table 24 may move the curing object K in the direction of the arrow F. Then, the gas N is jetted out of the gas outlets $A_{out}$ in the first direction D1 to the surface of the curing object K in order to remove the air on the surface of the curing object K. At the meanwhile, the UV light U generated by the UV light sources 232 of the UV module 23 is radiated in the first direction D1 after passing through the upper panel 211 and the lower panel 212.

Similarly, via the above mechanism, the air on the surface of the curing object K can be removed by the gas N jetted out of the gas outlets $A_{out}$ at the moment that the UV light U generated by the UV light sources 232 is radiated to the surface of the curing object K. Thus, the curing process of the ink on the surface of the curing object K would not be influenced by oxygen in the air, so the UV curing quality can be significantly improved.

As set forth above, the upper panel 211 and the lower panel 212 may be concave mirrors, convex mirrors, spherical mirrors, aspherical mirrors, etc. Therefore, the upper panel 211 and the lower panel 212 can also provide light condensing, light diffusing or other functions to appropriately adjust the UV light U generated by the UV light sources 232 in order to satisfy different requirements.

The UV device 2 in accordance with the embodiment can integrate the gas jetting module 21 with the UV module 23 by another design, which can also effectively inhibit oxygen in the UV curing process so as to optimize the UV curing quality thereof.

The embodiment just exemplifies the disclosure and is not intended to limit the scope of the disclosure. Any equivalent modification and variation according to the spirit of the disclosure is to be also included within the scope of the following claims and their equivalents.

Figure 8:
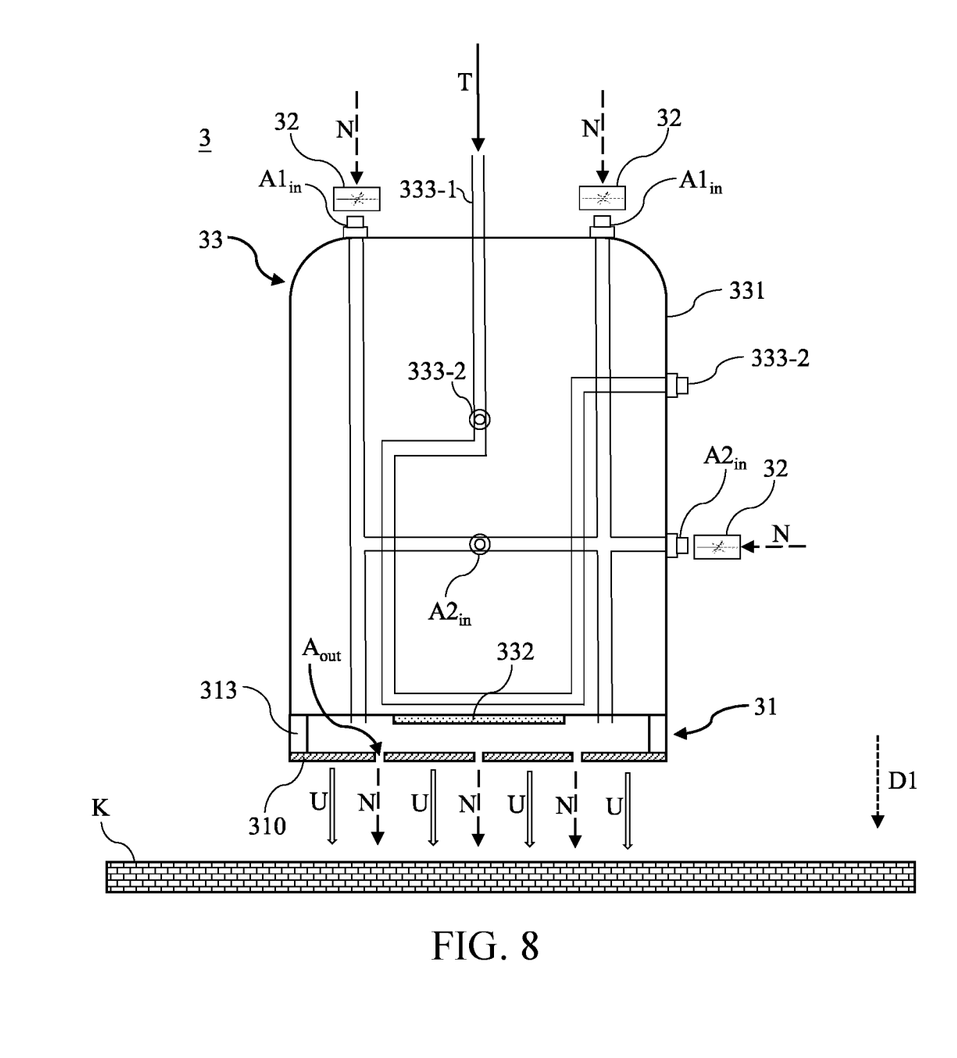
FIG. 8 is a front view of an UV device in accordance with a third embodiment of the disclosure.
Figure 9:
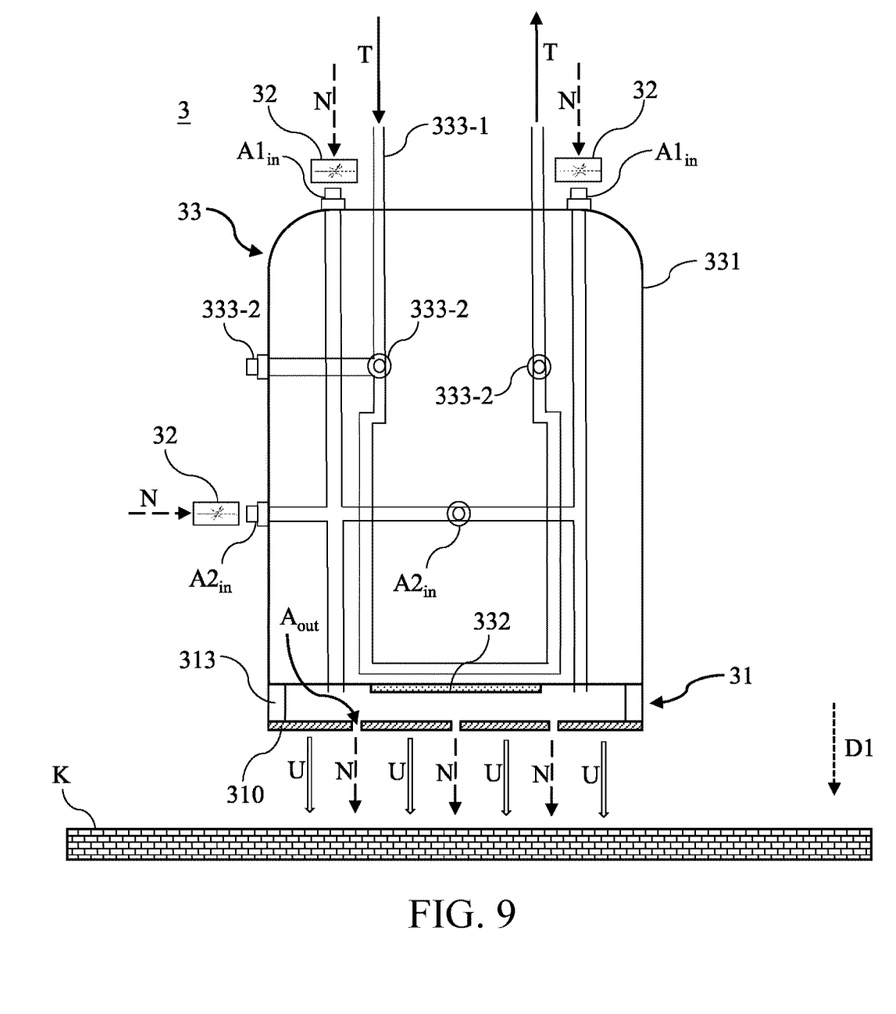
FIG. 9 is a side view of the UV device in accordance with the third embodiment of the disclosure.

Please refer to FIG. 8 and FIG. 9, which are a front view and a side view of an ultraviolet device in accordance with a third embodiment of the disclosure. As shown in FIG. 8 and FIG. 9, the ultraviolet (UV) curing device 3 includes a gas jetting module 31, a flow rate adjustment module 32 and an UV module 33.

The UV module 33 includes a housing 331, a plurality of UV light sources 332, a first coolant channel 333-1, a plurality of second coolant channels 333-2, a plurality of first gas channels $A1_{in}$ and a plurality of second gas channels $A2_{in}$. Similarly, the number of each of the above elements can be changed according to actual requirements. In another embodiment, the UV module 33 may have only one UV light source 332, one second coolant channel 333-2, one first gas channel $A1_{in}$ and one second gas channel $A2_{in}$, or have several first coolant channels 333-1.

The UV light sources 332 are disposed on the bottom of the housing 231 and may be arranged in straight line. In the embodiment, the UV light sources 332 may be UV LED arrays.

The first coolant channel 333-1 is disposed inside the UV module 33. The inlet and the outlet of the first coolant channel 333-1 are disposed on the top surface of the housing 331; besides, one end of the first coolant channel 333-1 extends from the top surface of the housing 331 into the inner space of the housing 331, and the other end of the first coolant channel 333-1 protrudes from the top surface of the housing 331. The second coolant channels 333-2 are disposed inside the UV module 33; besides, the second coolant channels 333-2 extend from the two sides (the two sides opposite to each other or adjacent to each other) of the housing 331 into the inner space of the housing 331 to connect to the first coolant channel 333-1 in order to serve as the inlets or outlets for the coolant T to flow in or out of. The UV module 33 can be effectively cooled by inputting the coolant T into the first coolant channel 333-1 and the second coolant channels 333-2. The UV light sources 32 and other relevant elements would generate a lot of heat, and the first coolant channel 333-1 and the second coolant channels 333-2 can effectively cool the UV light sources 332 and the other relevant elements, such that the UV module 33 can operate normally.

Each of the first gas channel $A1_{in}$ extends from the top surface of the housing 331 to the bottom surface of the housing 331. Thus, the inlet of each of the first gas channels $A1_{in}$ protrudes from the top surface of the housing 331 and the outlet of each of the first gas channels $A1_{in}$ protrudes from the bottom surface of the housing 331. The second gas channels $A2_{in}$ extend from the two sides (the two sides opposite to each other or adjacent to each other) of the housing 331 into the inner space of the housing 331 to connect to one or more of the gas coolant channels $A1_{in}$. Therefore, the gas N inputted into the second gas channel $A2_{in}$ can be exhausted from the outlets of the first gas channels $A1_{in}$.

The gas jetting module 31 includes a panel 310 and a frame 313. The panel 310 is disposed on the lower side of the frame 313 and the panel 310 includes a plurality of gas outlets $A_{out}$; the gas outlets $A_{out}$ are evenly distributed over the panel 310. In another embodiment, the UV device 3 may have only one gas outlet $A_{out}$; the number of the gas outlets $A_{out}$ can be changed according to actual requirements. The UV module 33 is disposed on the upper side of the frame 313, such that a gas chamber C is formed between the UV module 33, the panel 310 and the frame 313. The outlets of the first gas channels $A1_{in}$ are connected to the gas chamber C and the UV light sources 332 are disposed in the gas chamber C. Similarly, the panel 310 may be made of glass (e.g. quartz glass), other proper transparent materials or UV-pass materials. In the embodiment, the panel 310 may be a plane mirror. In another embodiment, the panel 310 may be a concave mirror, a convex mirror, a spherical mirror, an aspherical mirrors, etc.

The flow rate adjustment module 32 is connected to a gas storage tank (not shown in the drawings), the first gas channels $A1_{in}$ and the second gas channels $A2_{in}$. The gas storage tank inputs the gas N into the first gas channels $A1_{in}$ and the second gas channels $A2_{in}$, and the flow rate adjustment module 12 adjusts the flow rate of the gas N inputted into the gas channel C.

When the UV device 3 is activated, the gas N is jetted out of the gas outlets $A_{out}$ in the first direction D1 to the surface of the curing object K in order to remove the air on the surface of the curing object K. Meanwhile, the UV light U generated by the UV light sources 332 of the UV module 13 is radiated in the first direction D1 after passing through the panel 310.

Via the above mechanism, the air on the surface of the curing object K can be removed by the gas N jetted out of the gas outlets $A_{out}$ at the moment that the UV light U generated by the UV light sources 332 is radiated to the surface of the curing object K. Thus, the curing process of the ink on the surface of the curing object K would not be influenced by oxygen in the air, so the UV curing quality can be greatly improved.

As set forth above, the panel 310 may be a concave mirror, a convex mirror, a spherical mirror, an aspherical mirror, etc. Accordingly, the panel 310 can also provide light condensing, light diffusing or other functions to appropriately adjust the UV light U generated by the UV light sources 332 so as to satisfy different requirements.

The UV device 3 according to the embodiment has compact structure, so can be miniaturized. Therefore, the UV device 3 can be applicable to various small working spaces and can effectively enhance the UV curing quality.

The embodiment just exemplifies the disclosure and is not intended to limit the scope of the disclosure. Any equivalent modification and variation according to the spirit of the disclosure is to be also included within the scope of the following claims and their equivalents.

The UV devices in accordance with the embodiments of the disclosure can be applicable to various industries, such as printing industry (e.g. ink, varnish), optical communication industry (e.g. adhesive), electronic industry (e.g. adhesive, PCB solder mask), furniture industry (e.g. varnish), etc. Accordingly, the application of the UV devices can be more comprehensive.

Figure 10:
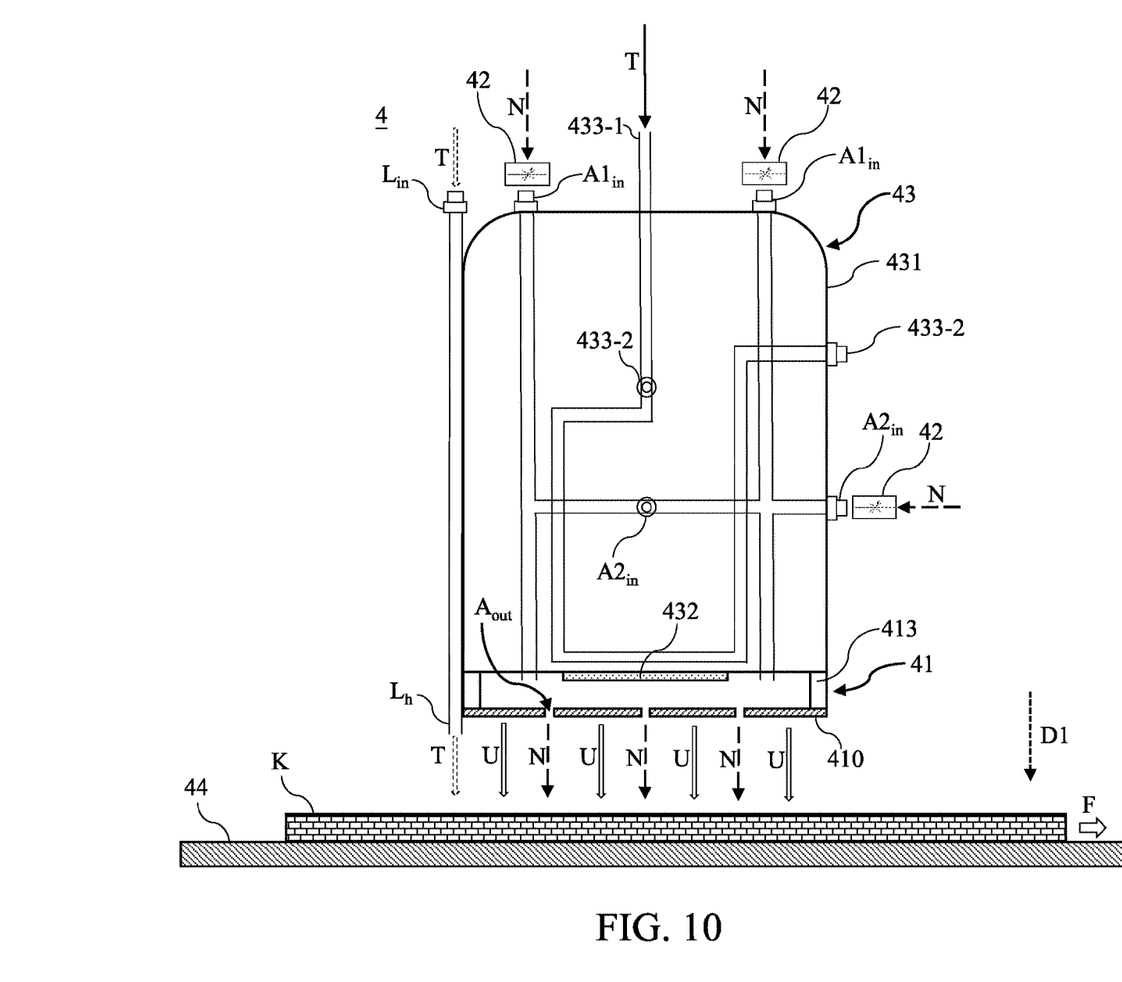
FIG. 10 is a first front view of an ultraviolet device in accordance with a fourth embodiment of the disclosure.

Please refer to FIG. 10, which is a first front view of an ultraviolet device in accordance with a fourth embodiment of the disclosure. As shown in FIG. 10, the UV device 4 includes a gas jetting module 41, a flow rate adjustment module 42 and an UV module 43.

The UV module 43 includes a housing 431, a plurality of UV light sources 432, a first coolant channel 433-1, a plurality of second coolant channels 433-2, a plurality of first gas channels $A1_{in}$ and a plurality of second gas channels $A2_{in}$.

The UV light sources 432 are disposed on the bottom of the housing 431 and may be arranged in straight line.

The gas jetting module 41 includes a panel 410 and a frame 413. The panel 410 is disposed on the lower side of the frame 413 and the panel 410 includes a plurality of gas outlets $A_{out}$; the gas outlets $A_{out}$ are evenly distributed over the panel 410.

The flow rate adjustment module 42 is connected to a gas storage tank (not shown in the drawings), the first gas channels $A1_{in}$ and the second gas channels $A2_{in}$.

The above elements are similar to the elements of the previous embodiment, so will not be described in this embodiment again. The difference between this embodiment and the previous embodiment is that the UV device 4 of this embodiment further includes a liquid channel $L_{in}$. The liquid channel $L_{in}$ may be disposed on or connected to one side of the UV module 43, and connected to a UV-curable liquid tank with a compressed gas as a gas carrier (not shown in the drawings). When the UV device 4 is activated, the working table 44 may move the curing object K in the direction of the arrow F. Then, the gas carrier with UV-curable liquid T (e.g. ink, varnish, etc.) is jetted out of the nozzle $L_h$ of the liquid channel $L_{in}$ in the first direction D1 to the surface of the curing object K. Afterward, the gas N is jetted out of the gas outlets $A_{out}$ of the panel 410 of the gas jetting module 41 in the first direction D1 to the surface of the curing object K in order to remove the air on the surface of the curing object K. Meanwhile, the UV light U generated by the UV light sources 432 of the UV module 43 is radiated in the first direction D1 after passing through the panel 410.

Via the above mechanism, the air on the surface of the curing object K can be removed by the gas N jetted out of the gas outlets $A_{out}$ at the moment that the UV light U generated by the UV light sources 432 is radiated to the surface of the curing object K. Thus, the curing process of the ink on the surface of the curing object K would not be influenced by oxygen in the air, so the UV curing quality can be greatly improved.

The UV device 4 of this embodiment can be further provided with the liquid channel $L_{in}$ capable of providing the UV-curable liquid T, so the UV device 4 can have more additional functions in order to satisfy the requirements of different applications. In another embodiment, the liquid channel $L_{in}$ may be disposed on the other side of the UV module 43. In still another embodiment, the UV device 4 may have two liquid channels $L_{in}$ disposed on both sides of the UV module 43. Therefore, the user can selectively activate one of the liquid channels $L_{in}$ according to the moving direction of the curing object K.

Figure 11:
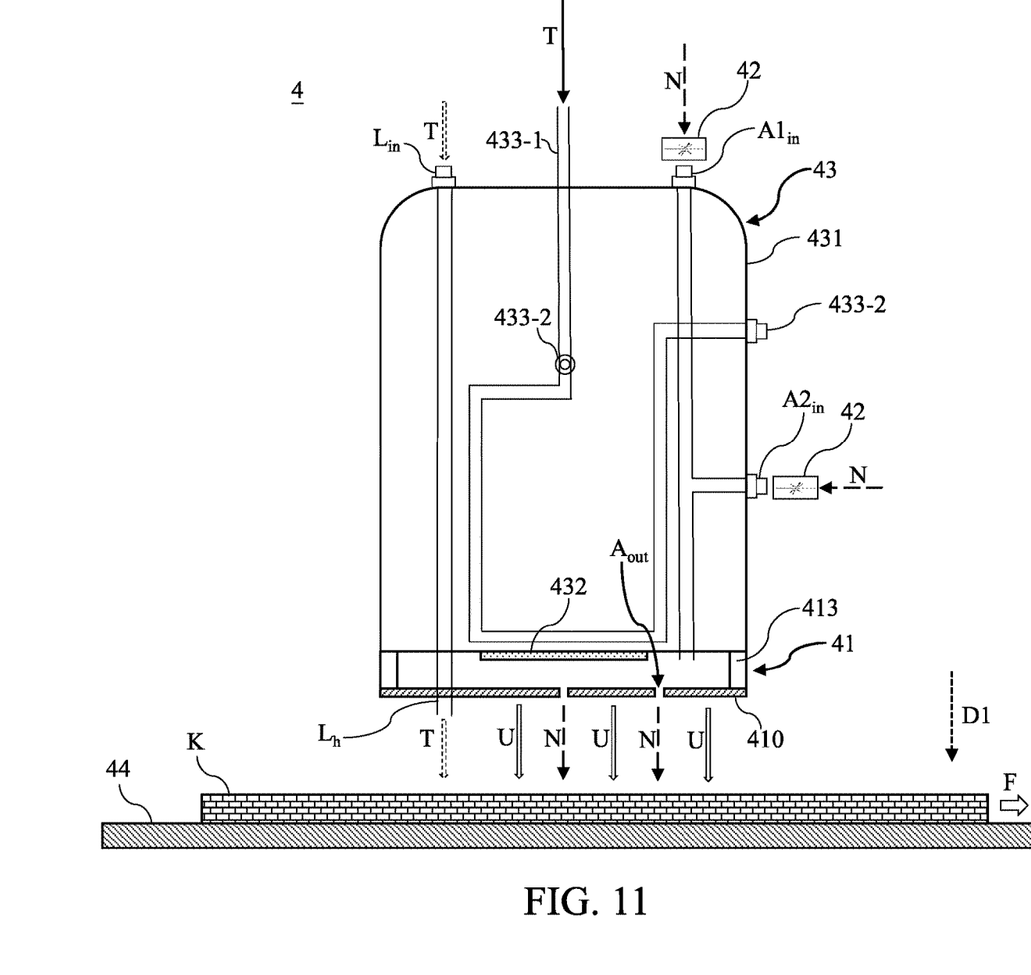
FIG. 11 is a second front view of the ultraviolet device in accordance with the fourth embodiment of the disclosure.

Please refer to FIG. 11, which is a second front view of the ultraviolet device in accordance with the fourth embodiment of the disclosure. As shown in FIG. 11, the liquid channel $L_{in}$ may be directly integrated with the UV module 43 and disposed inside the UV module 43.

Figure 12:
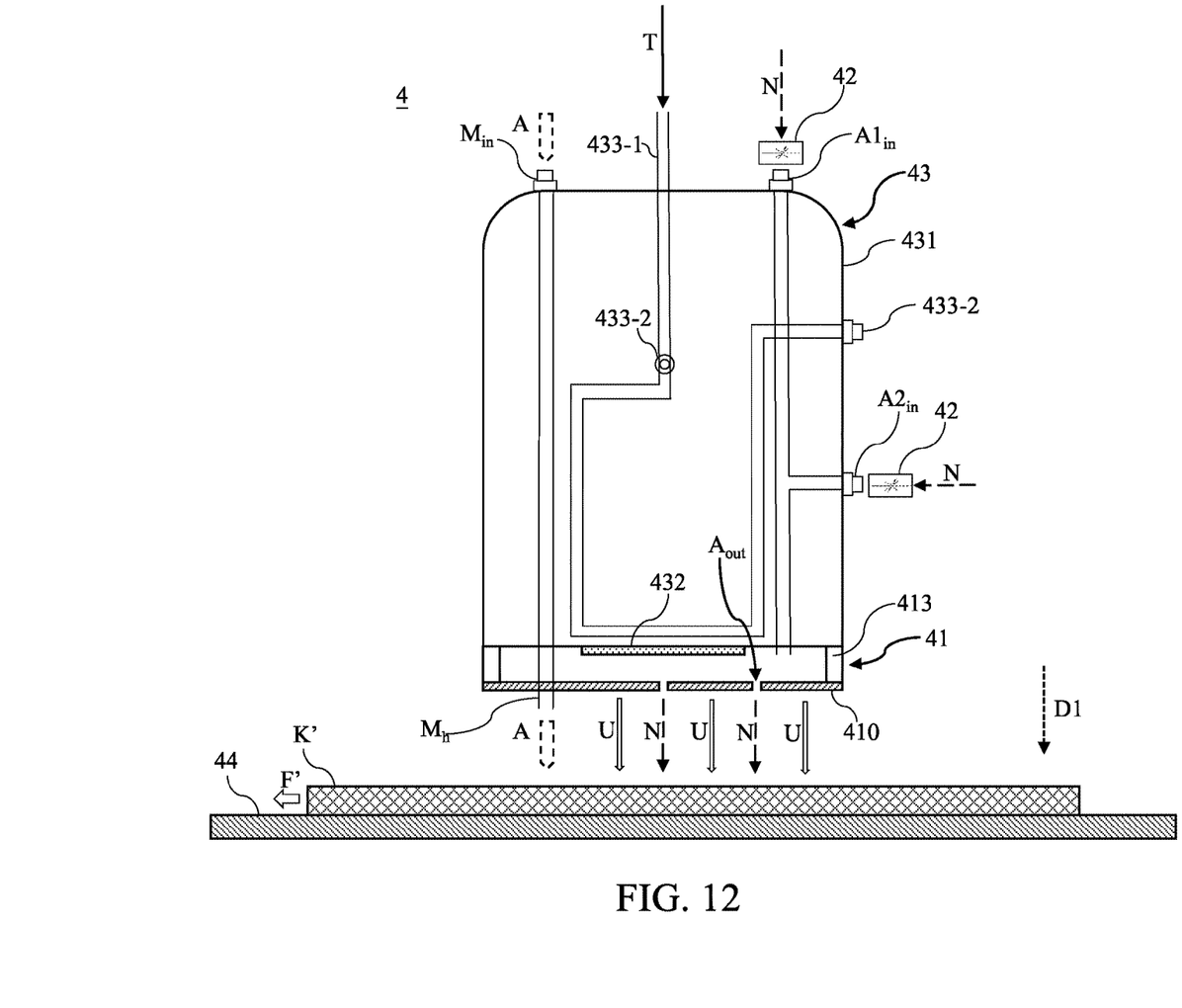
FIG. 12 is a third front view of the ultraviolet device in accordance with the fourth embodiment of the disclosure.

Please refer to FIG. 12, which is a third front view of the ultraviolet device in accordance with the fourth embodiment of the disclosure. As shown in FIG. 12, the liquid channel $L_{in}$ may be replaced by an antimicrobial agent channel $M_{in}$; the antimicrobial agent channel $M_{in}$ may be connected to an antimicrobial agent tank (not shown in the drawings). When the UV device 4 is activated, the working table 44 may move the curing object K in the direction of the arrow F'. Then, the gas N is jetted out of the gas outlets $A_{out}$ of the panel 410 of the gas jetting module 41 in the first direction D1 to the surface of the target object K' in order to agitate the air around the surface of the target object K'. Meanwhile, the UV light U generated by the UV light sources 432 of the UV module 43 is radiated in the first direction D1 after passing through the panel 410 with a view to disinfect the surface of the surface of the target object K'. Afterward, the antimicrobial agent A is jetted out of the nozzle $M_h$ of the antimicrobial agent channel $M_{in}$ in the first direction D1 to the surface of the target object K' so as to form an antimicrobial coating thereon.

As set forth above, the UV device 4 can be further provided with the antimicrobial agent channel $M_{in}$ capable of forming the antimicrobial coating on the surface of the target object K', so the UV device 4 can have more additional functions in order to satisfy the requirements of different applications.

The ultraviolet devices according to the above embodiments can be applied to various 2D surfaces and 3D surfaces.

Moreover, a same configuration of FIG. 12 can also be used for an advanced coating usage. The UV light sources 432 would be a UV-A/UV-C dual-output module or 2 individual UV modules. UV-C would be used to do disinfection on the surface of the object K and the surrounding area. At the same time, a curable antimicrobial agent would be purged from $M_h$ and reach the surface of the object K. UV-A and the gas N would then reach the surface of the object K to do UV curing on the curable antimicrobial coating.

In another embodiment, the configuration of FIG. 12 can be used for a non-curable anti-microbial agent. The UV light sources 432 would be a UV-C module. UV-C would be used to do disinfection on the surface of the object K and the surrounding area. At the same time, the antimicrobial agent would be purged from $M_h$ and reach the surface of the object K. Then, the antimicrobial coating would be formed with the UV disinfection for the surrounding area.

Besides, the ultraviolet devices shown in FIG. 8~FIG. 12 can be applied to not only curing ink or varnish, but also can be applied to curing other coatings. Further, as the ultraviolet devices shown in FIG. 8~FIG. 12 has compact structure, so the sizes thereof can be miniaturized to be several cubic centimeters. Therefore, these ultraviolet devices are applicable to various industries, such as electronics industry, optical communication industry, automobile industry, etc.

To sum up, according to one embodiment of the present disclosure, the UV device integrates the gas jetting module with the UV module by special design, so the UV device can effectively inhibit oxygen in the UV curing process in order to significantly improve the UV curing quality thereof.

Besides, according to one embodiment of the present disclosure, the UV device integrates the gas jetting module with the UV module by special design, and can directly jet out inert gas or inactive gas to the surface of the curing object in order to remove air on the surface of the curing object. Thus, the UV device can effectively inhibit oxygen without creating a closed-loop environment, so can achieve the desired technical effect in a cost-effective way.

Further, according to one embodiment of the present disclosure, the UV device integrates the gas jetting module with the UV module by special design, and provide inert gas or inactive gas via the gas jetting module, which can greatly reduce the consumption of inert gas or inactive gas. There, the UV device can achieve the desired technical effect in a cost-effective way.

Moreover, according to one embodiment of the present disclosure, the UV device integrates the UV light source with the first gas channel for inputting inert gas or inactive gas into one module, which can remarkably decrease the size of the UV module. Accordingly, the UV device can be applied to small working spaces.

Furthermore, according to one embodiment of the present disclosure, the UV device is applicable to various industries and can effectively enhance the UV curing quality in a cost-effective way. Thus, the application of the UV device can be more comprehensive.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An ultraviolet device, comprising:
   a gas jetting module, comprising an upper panel, a lower panel and a frame, wherein the upper panel is disposed on an upper side of the frame, and the lower panel is disposed on a lower side of the frame and comprises a gas outlet, and a gas chamber is formed between the upper panel, the lower panel and the frame;
   a first gas channel, connected to the gas jetting module and inputting a gas into the gas chamber;
   a flow rate adjustment module, connected to the first gas channel and configured to adjust a flow rate of the gas inputted into the gas chamber; and
   an ultraviolet module, comprising an ultraviolet light source, wherein the ultraviolet module is disposed on the gas jetting module and connected to the gas jetting module;
   wherein an ultraviolet light generated by the ultraviolet light source is radiated in a first direction after the ultraviolet light passes through the upper panel and the lower panel, and the gas is jetted out of the gas outlet in the first direction.

2. The ultraviolet device of claim 1, wherein the ultraviolet light source contacts the upper panel.

3. The ultraviolet device of claim 1, wherein the upper panel comprises an opening and the ultraviolet module is connected to the opening, whereby the gas chamber is formed between the ultraviolet module, the upper panel, the lower panel and the frame, and the ultraviolet light source is disposed in the gas chamber.

4. The ultraviolet device of claim 1, wherein the first gas channel is disposed on the upper panel in order to connect to the gas chamber.

5. The ultraviolet device of claim 1, wherein the ultraviolet module further comprises a housing, and the first gas channel extends from a top surface of the housing to a bottom surface of the housing, whereby an inlet of the first gas channel protrudes from the top surface of the housing, and an outlet of the first gas channel protrudes from the bottom surface of the housing and is connected to the gas chamber.

6. The ultraviolet device of claim 5, further comprising a second gas channel, wherein the second gas channel passes through an inner space of the housing, and extends from one side of the housing to the other side of the housing in order to connect to the first gas channel.

7. The ultraviolet device of claim 1, wherein the ultraviolet module further comprises a coolant channel for cooling the ultraviolet light source.

8. The ultraviolet device of claim 1, wherein the upper panel and the lower panel are made of a transparent material or an ultraviolet-pass material.

9. The ultraviolet device of claim 1, wherein the gas is an inert gas or an inactive gas.

10. The ultraviolet device of claim 1, wherein the upper panel and the lower panel are plane mirrors, concave mirrors, convex mirrors, spherical mirrors or aspherical mirrors.

11. The ultraviolet device of claim 1, further comprises a liquid channel connected to the ultraviolet module, wherein an ultraviolet-curable liquid is jetted out of a nozzle of the liquid channel in the first direction.

12. An ultraviolet device, comprising:
    a gas jetting module, comprising a panel and a frame, wherein the panel is disposed on a lower side of the frame and comprises a gas outlet;
    an ultraviolet module, comprising an ultraviolet light source and a first gas channel, wherein the ultraviolet module is disposed on an upper side of the frame, and a gas chamber is formed between the ultraviolet module, the panel and the frame; and
    a flow rate adjustment module, connected to the first gas channel and configured to adjust a flow rate of the gas inputted into the gas chamber;
    wherein an ultraviolet light generated by the ultraviolet light source is radiated in a first direction after the ultraviolet light passes through the upper panel and the lower panel, and the gas is jetted out of the gas outlet in the first direction.

13. The ultraviolet device of claim 12, wherein the ultraviolet light source is disposed in the gas chamber.

14. The ultraviolet device of claim 12, wherein the ultraviolet module further comprises a housing, and the first gas channel extends from a top surface of the housing to a bottom surface of the housing, whereby an inlet of the first gas channel protrudes from the top surface of the housing, and an outlet of the first gas channel protrudes from the bottom surface of the housing and is connected to the gas chamber.

15. The ultraviolet device of claim 14, further comprising a second gas channel, wherein the second gas channel extends from one side of the housing to an inner space of the housing in order to connect to the first gas channel.

16. The ultraviolet device of claim 14, wherein the ultraviolet module further comprises a first coolant channel, extending into the inner space of the housing, for cooling the ultraviolet light source, and an inlet and an outlet of the first coolant channel are disposed on the top surface of the housing.

17. The ultraviolet device of claim 16, wherein the ultraviolet module further comprises a second coolant channel extending from one side of the housing to the inner space of the housing so as to connect to the first coolant channel.

18. The ultraviolet device of claim 12, wherein the gas is an inert gas or an inactive gas.

19. The ultraviolet device of claim 12, wherein the panel is a plane mirror, a concave mirror, a convex mirror, a spherical mirrors or an aspherical mirror.

20. The ultraviolet device of claim 12, further comprises a liquid channel connected to the ultraviolet module, wherein an ultraviolet-curable liquid is jetted out of a nozzle of the liquid channel in the first direction.

* * * * *